(12) United States Patent
Cular et al.

(10) Patent No.: US 7,878,063 B1
(45) Date of Patent: Feb. 1, 2011

(54) SIMULTANEOUS SAMPLE MANIPULATION AND SENSING USING SURFACE ACOUSTIC WAVES

(75) Inventors: Stefan Cular, Albuquerque, NM (US); Venkat R. Bhethanabotla, Tampa, FL (US); Darren W. Branch, Albuquerque, NM (US)

(73) Assignees: University of South Florida, Tampa, FL (US); Sandia Corporation, Albuquerque, NM (US)

( * ) Notice: Subject to any disclaimer, the term of this patent is extended or adjusted under 35 U.S.C. 154(b) by 190 days.

(21) Appl. No.: 12/179,184

(22) Filed: Jul. 24, 2008

Related U.S. Application Data

(60) Provisional application No. 60/951,513, filed on Jul. 24, 2007.

(51) Int. Cl.
*G01N 29/024* (2006.01)
*G01N 29/036* (2006.01)

(52) U.S. Cl. .................. 73/579; 73/24.06; 73/29.02; 73/31.06; 73/61.79; 310/313 B; 310/313 D

(58) Field of Classification Search .......... 73/579, 73/24.06, 29.02, 29.05, 31.06, 61.79; 310/313 B, 310/313 D
See application file for complete search history.

(56) References Cited

U.S. PATENT DOCUMENTS

| | | | |
|---|---|---|---|
| 5,189,330 A | * | 2/1993 | Niitsuma ............... 310/313 B |
| 5,235,235 A | * | 8/1993 | Martin et al. ........... 310/313 D |
| 6,278,523 B1 | | 8/2001 | Gorecki |
| 7,052,854 B2 | | 5/2006 | Melker et al. |
| 2005/0106742 A1 | * | 5/2005 | Wahl ......................... 436/149 |

FOREIGN PATENT DOCUMENTS

| | | |
|---|---|---|
| WO | 2006010206 | 2/2006 |
| WO | WO 2009/061017 A1 * | 5/2009 |

OTHER PUBLICATIONS

Stefan Cular, Darren W. Branch, Grant D. Meyer, Harold Craighead, Venkat R. Bhethanabotla, "Removal of Nonspecific Binding on Microsensors Using Surface Acoustic Waves", 2005, downloaded from http://aiche.confex.com/aiche/2005/preliminaryprogram/abstract_31553.htm on Mar. 22, 2010.*

(Continued)

*Primary Examiner*—Hezron Williams
*Assistant Examiner*—Rose M Miller
(74) *Attorney, Agent, or Firm*—Courtney M. Dunn; Smith & Hopen, P.A.

(57) ABSTRACT

The present invention provides a hexagonal, delay line surface acoustic wave device fabricated on a a piezoelectric substrate, such as lithium tantalate, coated with an insulating waveguide on to which a sensing film, such as an anti-human Interleukin-6 biosensor film, is physically absorbed. The acoustic waves that propagate along the delay lines of the SAW device provide for detection of biological species along one delay line and simultaneously provide for removal of non-specifically bound protein along the remaining delay lines.

63 Claims, 7 Drawing Sheets

OTHER PUBLICATIONS

Anisimkin, I.V.; Anisimkin, V.I.; Gulyaev, Y.V.; Kryshtal, R.G.; Medved, A.V.; Phong, H.V.; Verona, E.; and Zemlyakov, V.E. Surface Acoustic Wave Sensors: New Analytical Capabilities. Vestnik Moskovskogo Universiteta, Khimiya. 41(6): 30-32, 2006.

Zheng, Y.; Biosensors on Surface Acoustic Wave Phononic Band Gap Structures. NNIN REU Research Accomplishments. 156-157, 2004.

Lec, R.M.; Lewin, P.A. Acoustic Wave Biosensors. Proceedings of the 20th Annual International Conference of the IEEE Engineering in Medicine and Biology Society. 20(6): 2779-2784, 1998.

Andle, J.C.; Vetelino, J.F. Acoustic Wave Biosensors. A: Physical Sensors and Actuators. 1:451-460, 1995.

Meyer, G.D.; Moran-Mirabal, J.M.; Branch, D.W.; Craighead, H.G. Nonspecific Binding Removal From Protein Microarrays Using Thickness Shear Mode Resonators. IEEE Sensors Journal. 6(2): 254-261. Apr. 2006.

Lange, K.; Voigt, A.; Rapp, M.; Karlsruhe, F. Surface Acoustic Wave Biosensors for Biomolecular Interaction Analysis. Institute for Instrumental Analysis. IEEE. 1174-1177, 2003.

Howe, H.L.; Wu, X.; Ries, L.A.G.; Cokkinides, V.; Ahmed, F.; Jemal, A.; Miller, B.; Williams, M.; Ward, E.; Wingo, P.A.; Ramirez, A.; Edwards, B.K. Annual Report to the Nation on the Status of Cancer, 1975-2003, Featuring Cancer Among U.S. Hispanic/Latino Populations. Cancer. 107(8): 1711-1742, Jul. 2006.

Cular, S.; Bhethanabotla, V.R.; Branch, D.W. Hexagonal Surface Acoustic Wave Devices for Enhanced Sensing and Materials Characterization. IEEE Sensors Journal, 2005.

* cited by examiner

SIMULTANEOUS SAMPLE MANIPULATION AND SENSING USING SURFACE ACOUSTIC WAVES

CROSS REFERENCE TO RELATED APPLICATIONS

This application claims priority to U.S. Provisional Patent Application No. 60/951,513, filed Jul. 24, 2007.

STATEMENT OF GOVERNMENT INTEREST

This invention was made with Government support under Grant No. 0221681 awarded by the National Science Foundation (NSF) and under United States Army Contact No. W81XWH-05-1-0585 awarded by the Department of Defense. The Government has certain rights in the invention.

FIELD OF INVENTION

This invention relates to a personal medical diagnostic device. More specifically, the device uses surface acoustic waves in the simultaneous removal of non-specifically bound proteins and detection of biological species.

BACKGROUND OF INVENTION

Surface Acoustic Wave (SAW) devices have been used both individually and in arrays as sensors and for materials characterization in a variety of applications ranging from gases/vapors to biological systems. Recently, the SAW device was developed. The hexagonal SAW permits rapid and simultaneous extraction of multiple film parameters of a thin film material, which achieves a more complete characterization than a single SAW device. In sensor applications, this capability allows for enhanced discrimination of an analyte and more accurate quantification. The design of the hexagonal SAW consists of three bi-directional SAW delay lines fabricated on a die. The delay lines are arranged about the center of the die and intersect at its center, producing a single region for sensor analysis. The central region where the acoustic waves intersect is shorted to reduce the number of modes of waves traversing the surface. In this manner, enhanced sensing and materials characterization is attained.

SAW devices have been used in many sensor applications in both gaseous and liquid environments. Each application has its own requirements. For example, the use of a SAW device as a biosensor implies that the device must not inherently be attenuated by the environment it operates in. This implication restricts SAW biosensors to Sheer Horizontal-SAW (SH-SAW) devices and a specialized SH-SAW device that creates a Love-mode wave from a thin film deposited on its surface.

SAW sensors work well as high sensitivity biosensors; however, as with all other biosensors, non-specifically bound (NSB) protein interactions can interfere with sensor response and concentration determination. NSB protein interaction can cause, among other problems, exaggerated response due to multi-layer formation, false responses due to miscellaneous proteins covering the surface, and no response due to poor alignment of the functional groups. Minor improvements to biosensor responses can be achieved by a thorough rinsing, use of ultrasonic baths, and pretreatment of the analyte containing fluids. However, each of these processes adds to the complexity of the creation and use of the biosensor and decreases the functionality of a biosensor operated without specialized training in everyday environments. Developments in acoustic wave applications have demonstrated NSB protein removal with relatively low power consumption thus significantly decreasing the uncertainty of the sensors response.

SAW devices known in the art lack the ability to remove NSB proteins while also detecting biological species. An improved sensor is needed in the art that provides simultaneous sensing and removal of NSB proteins. The improved sensor needs to improve sensitivity and selectivity while simultaneously removing NSB proteins. However, in view of the prior art considered as a whole at the time the present invention was made, it was not obvious to those of ordinary skill in the pertinent art how the identified need could be fulfilled.

SUMMARY OF INVENTION

The need for a biosensor that exhibits desired characteristics superior to biosensors known in the art is now met by a new, useful, and non-obvious invention.

In accordance with the present invention is provided a biosensor including a surface acoustic wave (SAW) device fabricated on a piezoelectric substrate and an insulating waveguide positioned on the SAW device, the waveguide further comprising a bio-sensing film.

In a preferred embodiment, the piezoelectric substrate is a lithium tantalite substrate. However, other piezoelectric substrates, such as lithium niobate, are within the scope of the present invention.

In a preferred embodiment, the insulating waveguide is a polystyrene waveguide. However, waveguides consisting of other materials are within the scope of the present invention In a preferred embodiment, the SAW device is a hexagonal SAW device. However, SAW devices designed and fabricated to have a different shape are within the scope of the present invention.

Additionally, in another embodiment, the SAW device further comprises three delay lines: a first delay line lying along the on-axis direction (36° YX LiTaO$_3$) and two delay lines, which lie along the off-axis direction. However, devices comprising a different number of delay lines and in other directions are within the scope of the present invention. In addition, the delay lines in accordance with the present invention preferably lie along each Euler direction. The delay lines may be shorted and may be bi-directional.

The delay lines in accordance with the present invention may comprise two ports. The two ports may each comprise an inter-digital transducer, wherein the design of the inter-digital transducer may be selected from the group consisting of double split finger, pruned double split finger, or unidirectional. This is not meant to be limiting and other inter-digital transducer designs are within the scope of the present invention. In addition, the inter-digital transducers may have a length of 197λ and an aperture of 47λ. However, this is not meant to be limiting and other lengths and apertures are within the scope of the present invention. Each inter-digital transducer comprises a plurality of inter-digital transducers finger pairs, wherein the finger pairs may have a periodicity of 40 microns and an aperture width of 200 microns.

A power source is applied to the SAW device results in the propagation of acoustic waves along each of the on- and off-axis directions. In a preferred embodiment the power level is about 12 mW; however, this is not meant to be limiting and other voltages are within the scope of the present invention. The acoustic waves propagating along the on-axis direction may be different from the acoustic waves propagating along the off-axes directions. In a preferred embodiment, a wave chosen from the group consisting of shear horizontal SAWs and Love SAWs propagates along the on-axis direction, which enables biological species detection along that direction. An ellipsoidal wave, corresponding closely to a Rayleigh mode wave, propagates along the off-axis directions enabling removal of non-specifically bound proteins. Accordingly, the device provides for simultaneous surface manipulation and biological species detection.

Additionally, the SAW device may be used to detect Interleukin-6(IL-6) at low physiologically important values. This can be achieved by using an anti-human Interleukin-6 biosensor film as the sensing film. However, this is not meant to be limiting and the detection of other biological species and use of other sensing films are within the scope of the present invention.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The present invention is based on the finding that non-specifically bound (NSB) protein removal and biological species detection can be achieved simultaneously by ultrasonic waves with relatively low power consumptions.

Acoustic waves can be generated in piezoelectric materials. The piezoelectric material may be either a polished substrate such as quartz, lithium niobate, lithium tantalite, or a thin film such as zinc oxide. Quartz is the most commonly used substrate because of its temperature stability for certain crystal orientations. However, for high acousto-electric couplings lithium tantalate is preferred over quartz, because it allows for the efficient transfer of energy from electrical to mechanical form. The crystal orientation, the thickness of the piezoelectric material, and the geometry of the metal transducers determine the type and mode of the acoustic waves.

Figure 1:
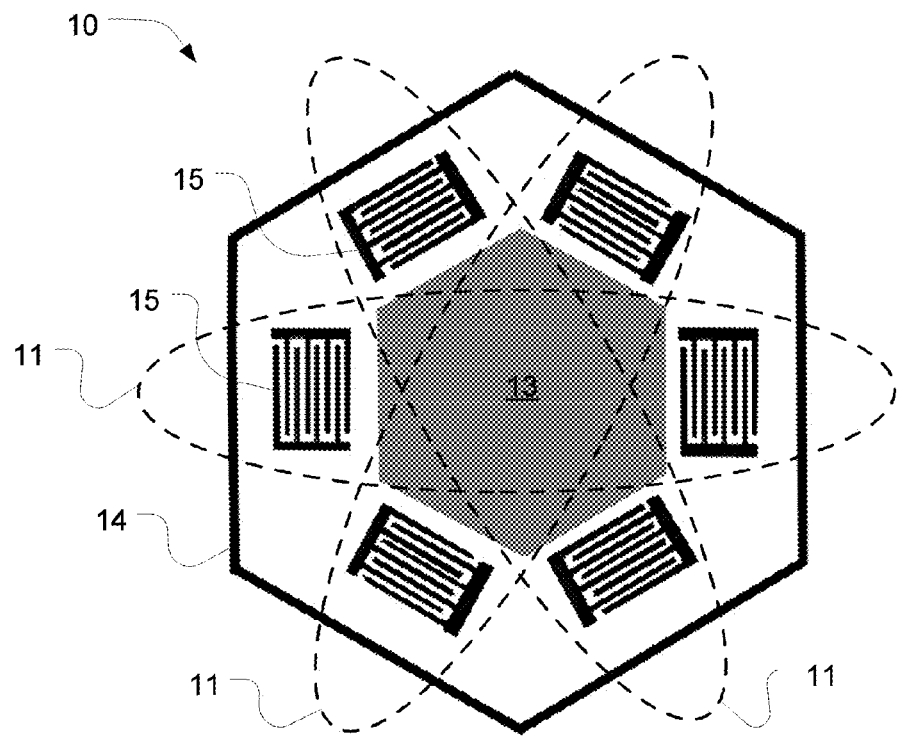
FIG. 1 is a diagram of the hexagonal SAW device in accordance with an embodiment of the present invention.

In hexagonal surface acoustic wave (SAW) device 10, as shown in FIG. 1, three delay lines 11 generate SAWs using inter-digital transducers (IDTs) 15 patterned on substrate 14. Each delay line 11 has two IDTs 15. One IDT 15 of each delay line 11 is used as a transmitter that converts an applied voltage variation into acoustic waves and the other IDT 15 receives these acoustic waves and converts them back to an output voltage. Delay lines 11 are identical and bi-directional. Delay lines 11 are also arranged about the center of substrate 14 and intersect at its center, producing a single region for sensor analysis. The central region where the acoustic waves intersect is shorted to reduce the number of modes of waves traversing the surface.

Figure 2A:
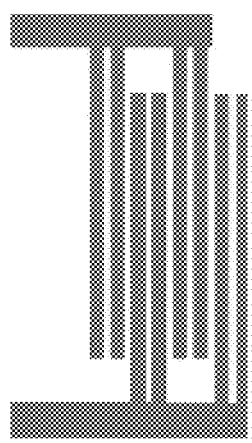
FIG. 2A is a diagram of a double split finger inter-digital transducer design in accordance with an embodiment of the present invention.
Figure 2B:
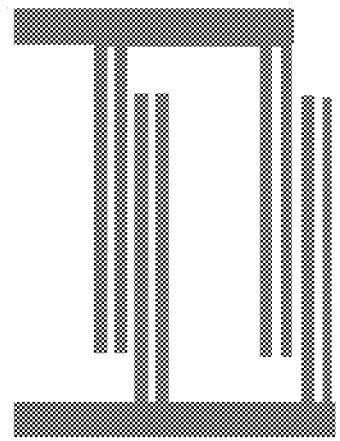
FIG. 2B is a diagram of a pruned double split finger inter-digital transducer design in accordance with an embodiment of the present invention.
Figure 2C:
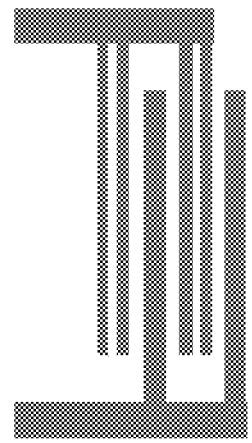
FIG. 2C is a diagram of a unidirectional double split finger inter-digital transducer design in accordance with an embodiment of the present invention.

The layout and dimensions of IDT 15 control the period and other attributes of the surface wave. There are three IDT designs of interest: double split finger (DSF), pruned double split finger (PR-DSF), and unidirectional double split finger (U-DSF). The DSF design, shown in FIG. 2A, is the traditional design. The PR-DSF design, shown in FIG. 2B, is a enhanced version of the DSF design. Every other finger pair is removed from the DSF design to create the PR-DSF design. This design maintains the lower insertion loss of a standard DSF transducer with the equivalent number of finger pairs, but has a narrower pass band. The PR-DSF design also reduces the internal reflections that would occur in a traditional DSF design having the full amount of finger pairs. The unidirectional design, shown in FIG. 2C, employs a weighting technique of using one finger followed by a split finger to create the finger pair. This design generates waves that are directional, thus sending more energy across the delay line. This design is also referred to as a single-phase unidirectional transducer (SPUDT) and has the advantage of low interfering reflections and low insertion loss.

Figure 3:
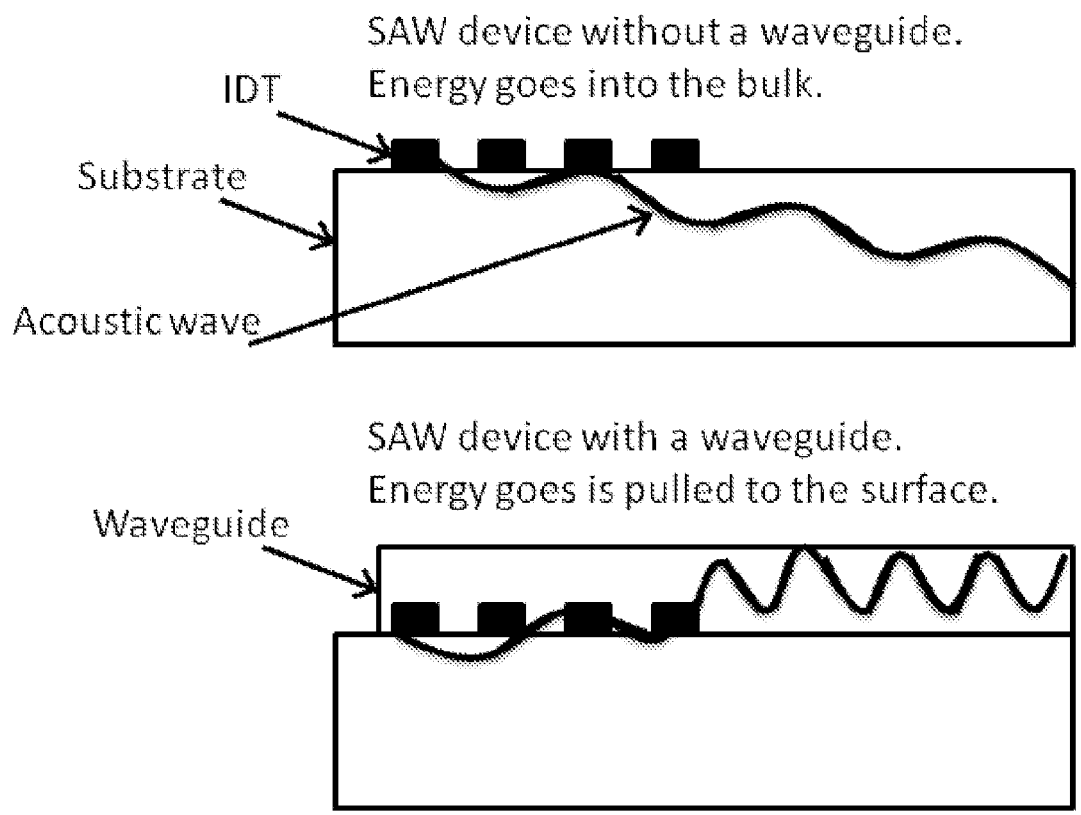
FIG. 3A is a diagram illustrating a SAW device without a waveguide.
FIG. 3B is a diagram illustrating a SAW device with a waveguide.

In an exemplary embodiment, with reference to FIG. 1, the biosensor of the present invention includes hexagonal SAW device 10 with three delay lines 11, as previously described. In this embodiment, the delay lines 11 are fabricated on 36° lithium tantalite substrate 14, which allows for propagation of both Rayleigh and shear horizontal (SH) wave modes simultaneously. Once delay lines 11 are fabricated on substrate 14, substrate 14 is spin-coated with a polymer waveguide. A bio-sensing film is then physically absorbed on to the waveguide. The waveguide is illustrated in FIGS. 3A and 3B.

The choice of a delay line for sensing and simultaneous cleaning depends on the propagation characteristics of the wave generated along the crystal cut and orientation corresponding to that delay line. In a preferred embodiment of the present invention, one delay line is used for biological species detection and the other two delay lines are used to remove the NSB proteins. Each delay line lies along a Euler direction. The delay line used for sensing is located along the on-axis direction (36° YX LiTaO3). The on-axis direction is used because the wave that propagates along it has a significant shear horizontal (SH) component and SH-SAWs are suitable for sensing applications. The waves propagating along the off-axis directions have mixed-modes with a dominant Rayleigh wave component. Rayleigh waves function to remove NSB proteins.

Figure 4A:
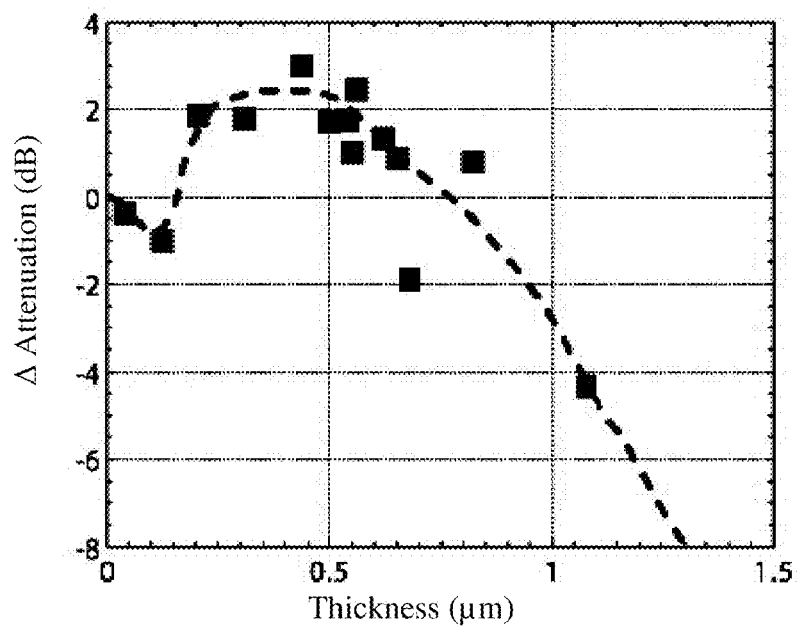
FIG. 4A illustrates the change in attenuation for varying thicknesses of the polystyrene waveguide, showing optimization at a thickness of about 0.5 µm in accordance with an embodiment of the present invention.
Figure 4B:
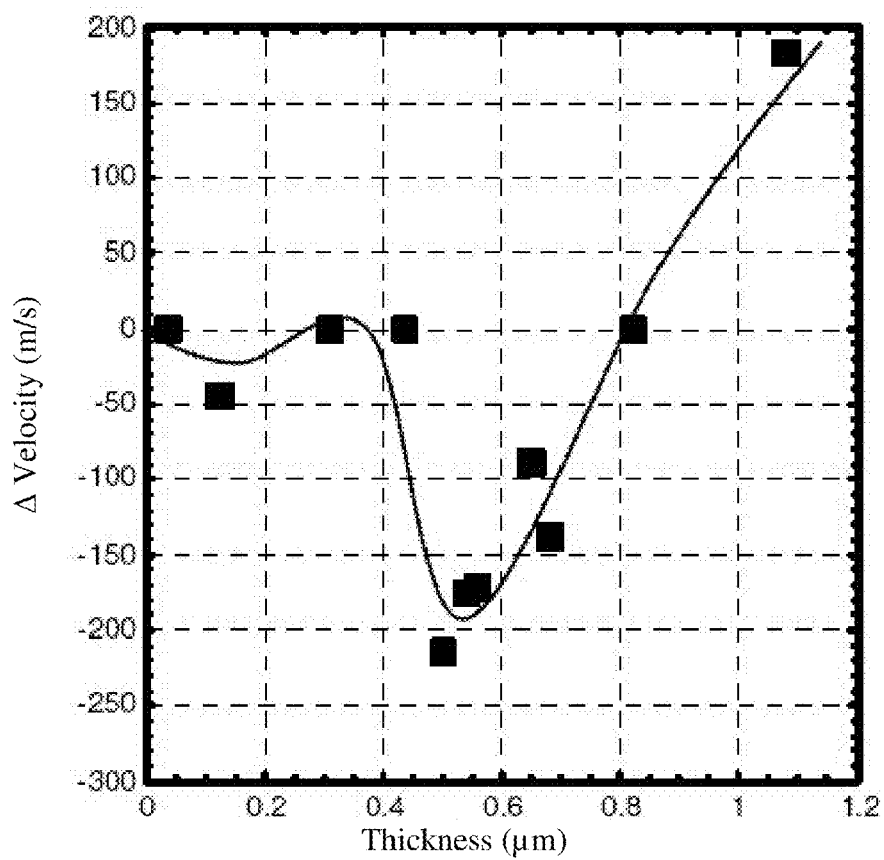
FIG. 4B illustrates the change in velocity for varying thicknesses of the polystyrene waveguide, showing optimization at a thickness of about 0.5 µm in accordance with an embodiment of the present invention.

To increase sensitivity to perturbations Love waves may be propagated along the on-axis direction. Love-waves are SAWs having a horizontal motion that is transverse (or perpendicular) to the direction the wave is traveling. Love-wave sensors can be twenty times more sensitive to perturbations than the corresponding SH-SAW sensor. Generation of Love-waves is achieved through use of a waveguide of appropriate material and thickness. Polystyrene is a preferred material in bio-sensing applications because it has low water permeability, is nontoxic, and has a robust structure to withstand multiple uses. A polystyrene waveguide thickness of about 0.5 µm produced highest attenuation, as shown in graphs of FIG. 4. FIG. 4A shows the change in attenuation for varying thickness of the waveguide and FIG. 4B shows the change in velocity for varying thickness of the waveguide.

In an additional embodiment, the biosensor of the present invention includes a SAW device fabricated on a piezoelectric substrate, an insulating waveguide positioned on the SAW device, and a sensing film positioned on the waveguide. The SAW device comprises at least two delay lines, one capable of propagating either SH-SAWs or Love SAWs and the other capable of propagating a wave that is substantially ellipsoidal. The delay lines are fabricated to intersect such that the area of intersection allows for both NSB protein removal by the substantially ellipsoidal waves and bio-sensing by either the SH-SAWs or Love SAWs. The piezoelectric substrate may consist of lithium tantalate or lithium niobate. The waveguide may consist of a polystyrene waveguide. However, these materials are not meant to be limiting and other substrate and waveguides are within the scope of the invention.

The features and advantages of the invention are more fully illustrated by the following non-limiting examples.

Example 1

FIG. 1 provides a schematic of hexagonal SAW device 10. As shown, hexagonal SAW device 10 is a composite of three traditional delay lines 11 arranged about the center of the substrate die 14, which is approximately 20 mm×20 mm. The individual delay lines 11 are comprised of identical bi-directional IDTs 15 with an aperture of 47λ, delay length of 197λ, and feature size of 4 µm. The delay line is shorted to eliminate unwanted waves and eliminate the electrical effect. A standard metallization procedure of 100 nm titanium adhesion layer followed by 700 nm gold layer is used.

Sensitivity required for detection of many biological markers is on the order of a few nano-grams per milliliter, which is obtainable by many types of sensors; however, SAW sensors are some of the most sensitive and easy to implement devices. Challenges associated with this order of mass sensitivity become largely a fixture and test parameter issue because any variation in fluid flow or pressure will cause a significant sensor response. Therefore, a precision syringe pump (Harvard Apparatus PHD 2000), which, unlike peristaltic pumps, provides a smooth continuous flow with no pulses. A LabView® virtual instrument interface that controls and records all electronic operations including flow rate, flow direction, and valve position is used to simplify configuration and operation of the test bed.

Figure 5A:
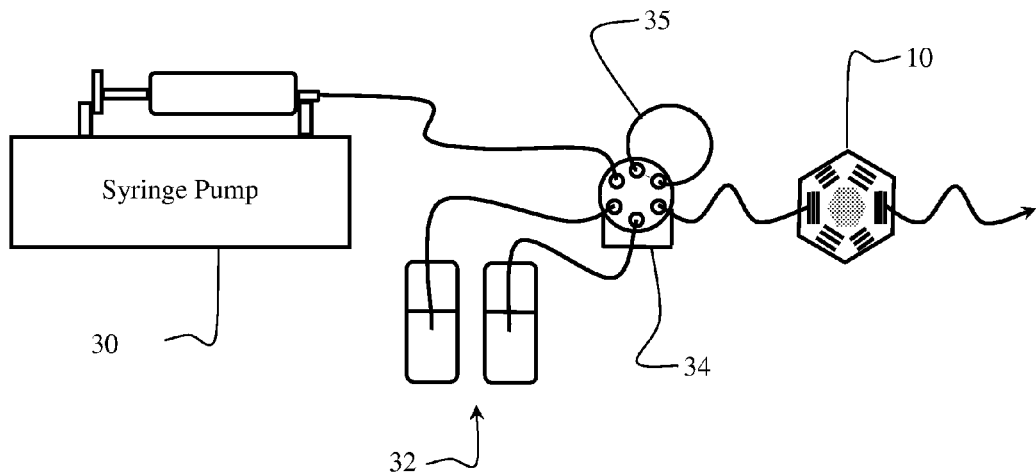
FIG. 5A is a schematic of an equipment set-up for liquid phase sampling of biologic samples in accordance with an embodiment of the present invention.
Figure 5B:
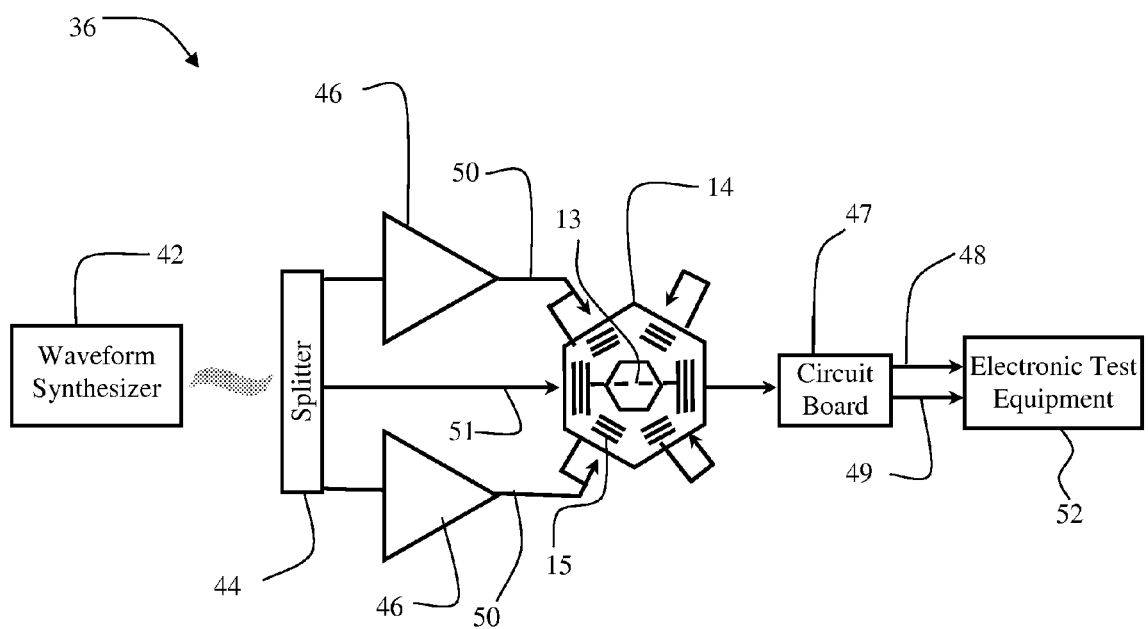
FIG. 5B is a schematic of a microfluidic test bed for liquid phase sampling of biologic samples in accordance with an embodiment of the present invention.

The equipment set-up is shown in FIG. 5A. As shown, test samples 32 and syringe pump 30 are regulated by a multi-port valve 34 with flow loop 35. Multi-port valve 34 is controls the flow of the samples to micro-fluidic test fixture 36. Due to the design of the hexagonal SAW device, a typical micro-fluidic fixture is not feasible; therefore, custom test fixture 36 was designed and fabricated. Test fixture 36 is constructed of polycarbonate, which has low moisture absorption, high strength, no centerline porosity, easy machine-ability, and can be polished to be optically clear. Test fixture 36, shown in detail in FIG. 5B, synthesizes a waveform 42 which is then split equally 44 into three waveforms. Two waveforms are amplified by power amplifiers 46 and third waveform 51 remains unchanged. Amplified waveforms 50 are introduced to IDTs 15 of the two delay paths in the off-axis direction. Amplified waveforms 50 are used by IDTs 15 of the two delay paths to propagate a wave that will have a large enough amplitude to perturb central sensing region 13 enough to remove NSB proteins and other loosely bound materials. Unchanged waveform 51 is introduced to IDT 15 of the delay path in the on-axis direction and used to propagate a sensing wave. A printed circuit board 47 with SMA connectors is connected to electronic test equipment 52. The circuit board 47 determines change in phase 48 and change in magnitude 49 of the sensing wave and outputs this data to the electronic test equipment 52.

The hexagonal SAW devices were designed for biosensor applications; however, additional preparations of the sensor-surfaces are necessary. The IDTs must be insulated from the liquid environment by the application of a waveguide. The insulating material must not attenuate the SAWs excessively, must not be highly permeable to water, and must permit attachment of antibodies. Therefore, high molecular weight polystyrene (Sigma Aldrich) is used as the insulating material. Coating of the device is achieved by dissolving polystyrene in 2-butoxyethyl acetate (Sigma Aldrich) to four weight percent then spin coating the device with the mixture. The devices are then annealed at 120° C. for one hour.

Following the annealing, the devices were mounted in micro-fluidic test fixture 36 and characterized using a vector network analyzer (Agilent 8753ES). From a calculated exposed area of the sensor surface and cross-sectional areas of the antibodies used, a concentration of proteins was specified to ensure complete coverage of the sensor surface without excessive multi-layer formation of NSB proteins. The calculated protein concentration was applied to the surface of the sensor through micro-fluidic test fixture 36 for one hour to allow adequate surface adsorption to the polystyrene. Having the sensor functionalized with an antibody, goat anti-mouse IgG (Pierce), varying concentrations of antigen, mouse anti-rabbit IgG (Pierce) was flowed across the sensor at a constant 0.15 ml/min. The antigen concentrations were calculated and made to ensure less than 25% surface coverage. To ensure a good response of the sensor, a pH of 7.4 was maintained by using of phosphate buffered saline (PBS) solution.

High amplitude waves were used to remove loosely bound materials from the sensors surface. To view surface manipulation, a Leica DM14000 fluorescent microscope was used. With the prepared sensors, fluorescently labeled proteins were adsorbed onto the surface of the device for one hour to achieve saturation. Sensors where then flushed with three ml of PBS. Following the flushing, the devices were subjected to high amplitude waves using a 4-watt RF power amplifier (Mini-Circuits TIA-1000-1R8). The actual power delivered to the IDT was on the order of milli-watts due to insertion loss of the device and attenuation by the films on the surface.

The high amplitude waves manipulating the surface and the use of low amplitude waves for sensing changes in the sensing film was then done simultaneously. The sensors were first prepared with an antibody film as described above, and used to sense a known concentration of antigen in solution. After the sensing test, the sensors were coated with known concentrations of a NSB protein, Bovine Serum Albumin (BSA). Following the BSA application, the sensors were flushed with three ml of PBS then subjected to high amplitude waves while monitoring the changes with a different delay line.

Figure 6:
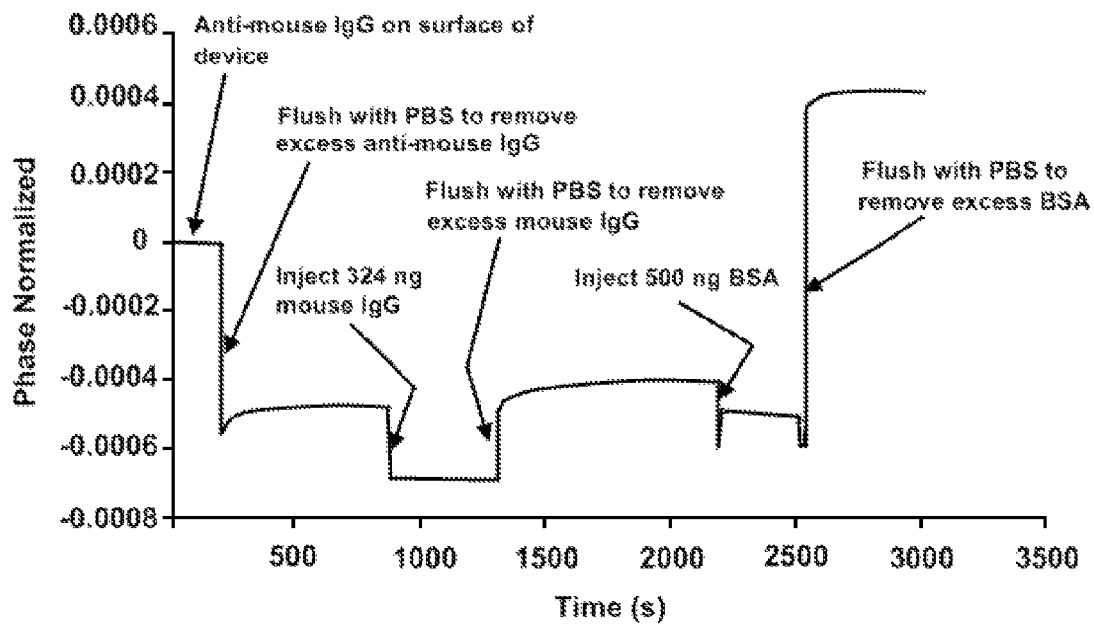
FIG. 6 is a diagram of the normalized phase response for the coating of a sensor with antibodies (138 ng/ml anti-mouse IgG in PBS) followed by the detection of the antigen (324 ng mouse IgG), and the coating of the sensor with non-specifically binding BSA (500 ng).

The biosensor is capable of detecting nano-grams of mass change on their surfaces. This was demonstrated with the detection of low levels of mouse IgG binding with a functionalized surface. A representative data set of the sensing capability is shown in FIG. 6. The first drop in the graph is the result of flushing away the excess antibody from the one hour adsorption process. Following the first large drop, the antigen is injected and flushed away. In this event, there are two significant measurements. First, the phase change upon injecting a known concentration sample, and second, the non-returning of the phase change value to the baseline (residual difference in phase change) even after extensive flushing with PBS. The large step-up seen upon flushing the system with PBS to remove the excess BSA appears to be removal of the BSA, but attenuation measurements show that it is, instead, a complex non-linear response upon the adhesion of a large amount of BSA.

In the next step, BSA is injected to completely coat the surface in preparation for the NSB protein removal. The magnitude of this response is significantly different from the response of the specific antigen, which is the result of leaving the linear response regime of the SAW sensor by applying too much material onto the surface. For many biosensors, this would result in having to discard the sensor and start over with a new one. However, for the biosensor of the present invention this allows for demonstration of the simultaneous manipulation and sensing functions.

Figure 7:
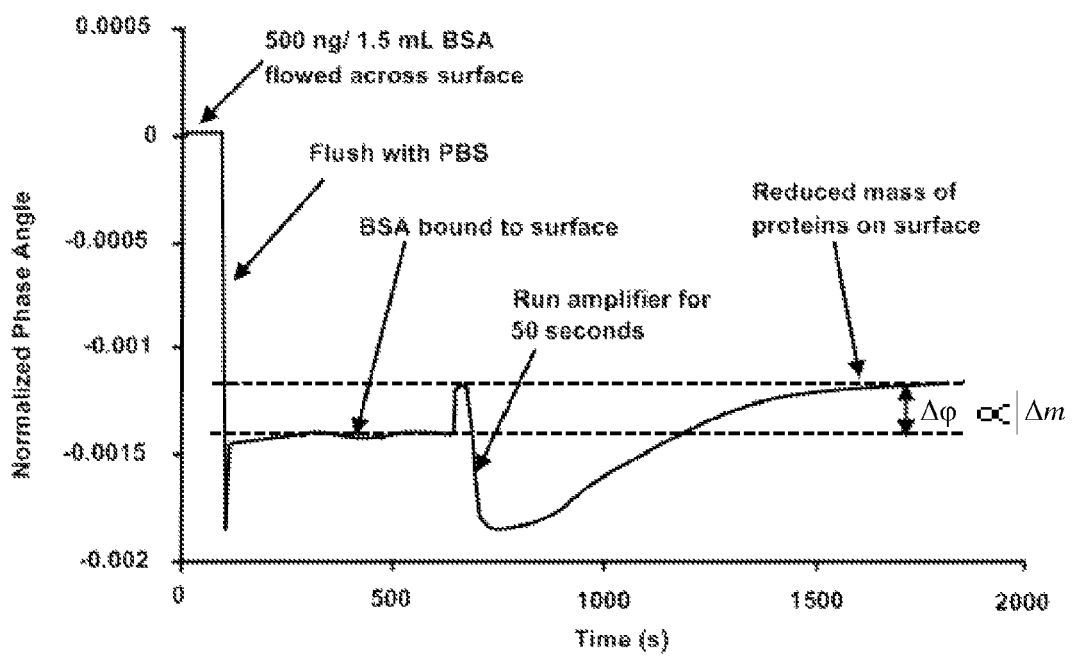
FIG. 7 is a diagram of the normalized phase angle response of sensor to the removal of excess BSA with just PBS followed by the removal of NSB BSA using high amplitude waves.

It is common to not have a pure sample of the analyte protein of interest. Such a sample requires extensive filtering and/or processing before a concentration determination with the sensor. The graph shown in FIG. 7 demonstrates the simultaneous sensing and manipulation of the sensing film using two types of SAWs propagating in different directions. The graph shows the addition of a high concentration of BSA to the surface of the SAW sensor followed by the removal of some of the BSA remaining on the surface upon extensive flushing with PBS. Further removal is achieved through the application of the power amplified signal for 50 seconds on a different SAW delay line than that used for sensing.

Example 2

Hexagonal SAW device 10 is a composite of three traditional delay lines 11 arranged about the center of 36° YX LiTaO$_3$ substrate die 14. The die 14 dimensions are approximately 20 mm×20 mm×0.5 mm. The individual delay lines 11 are comprised of identical bi-directional IDTs 15 with an aperture of 47λ and delay length of 197λ. Each IDT contains thirty finger pairs. The periodicity of the finger pairs is 40 microns and the aperture width is 200 microns. The transmitting and receiving IDTs are spaced 3.25λ apart. The delay line is shorted to eliminate unwanted waves and eliminate the electrical effect. A standard metallization procedure of 100 nm titanium adhesion layer followed by 700 nm gold layer is used.

Upon fabrication of the IDTs on the lithium tantalite substrate, the waveguide is applied by spin coating the device with four weight-percent polystyrene in butoxyethyl acetate. The optimal thickness of the polystyrene is about 0.5 μm, which enables Love-wave generation. The polymer waveguide is annealed for one hour at 120° C.

Figure 8:
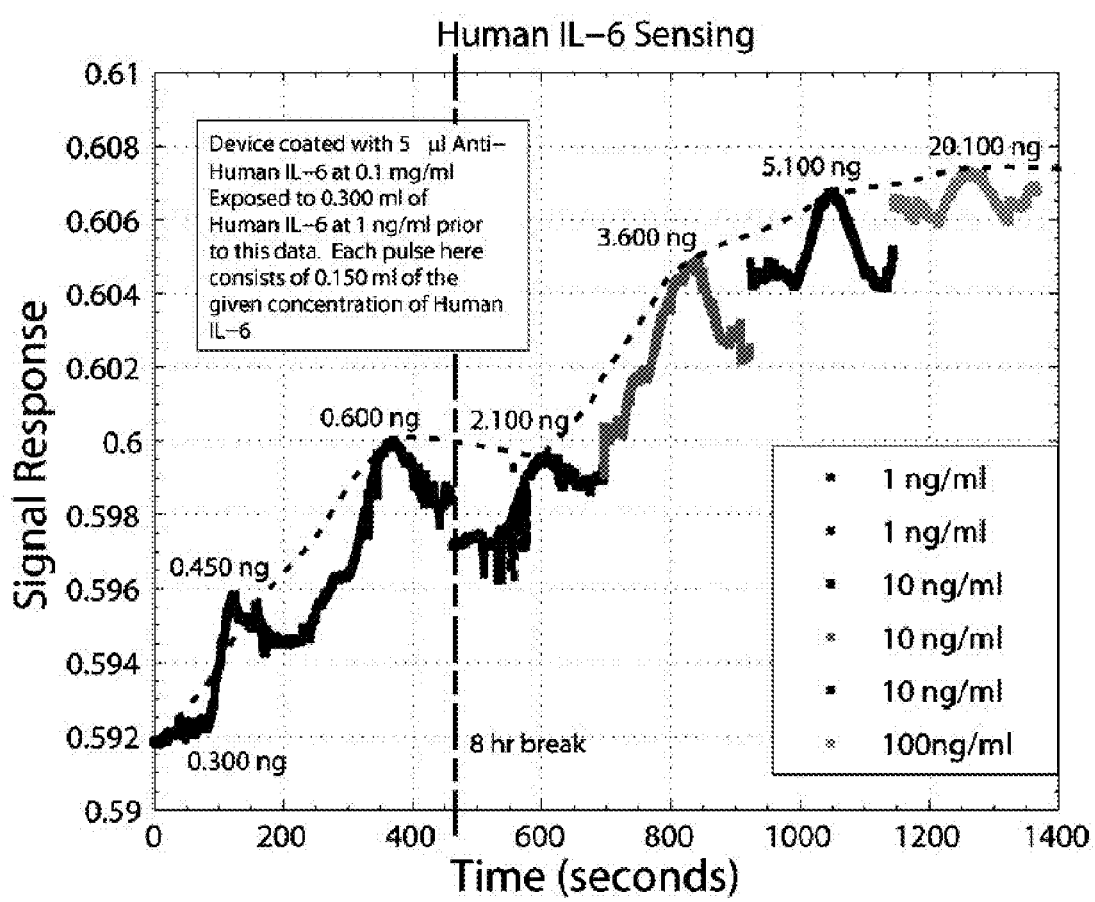
FIG. 8 illustrates the signal response over time of Interleukin-6 in accordance with an embodiment of the present invention.
Figure 9:
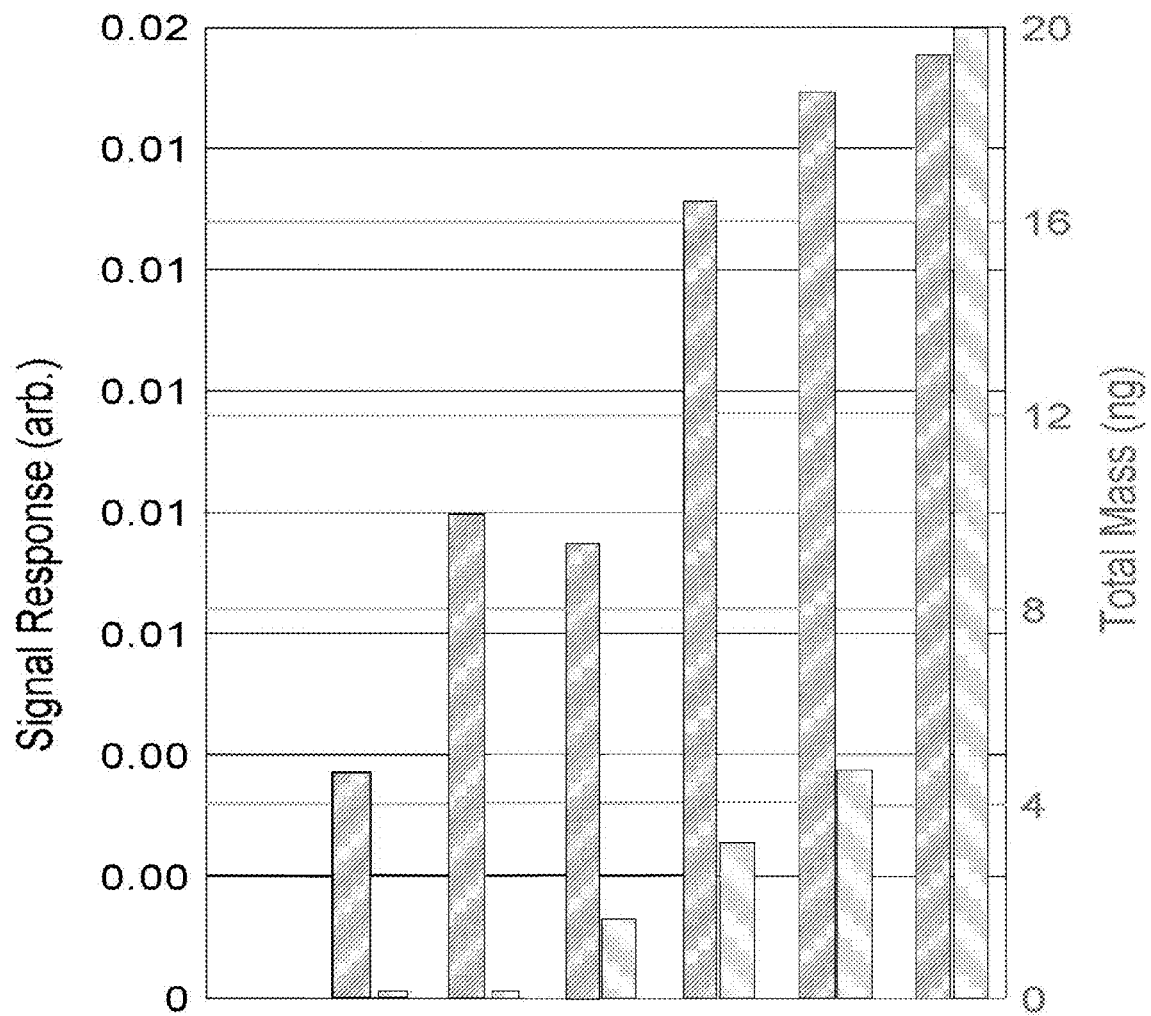
FIG. 9 compares the signal response of Interleukin-6 with total mass in accordance with an embodiment of the present invention.

An anti-human Interleukin-6 biosensor film is then physically absorbed to the polystyrene waveguide. Interleukin-6 is a pro-inflammatory cytokine involved in the body's pathophysiologic response to injury due to various causes, e.g. trauma, burns, sepsis, and disease. Using the experimental setup shown in FIGS. 5A and 5B, the saturation data, shown in FIGS. 8 and 9, for sensing Interleukin-6 in buffer solution with increasing quantities injected was collected.

As shown by these exemplary embodiments, a biosensor is provided having improved characteristics over other sensors known in the art. The present invention provides a delay line SAW device fabricated on an piezoelectric substrate having an insulating waveguide positioned thereon, which allows for simultaneous removal of NSB proteins and biological sensing by the propagation of differing waves along the different delay lines of the device.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described, What is claimed is:

1. A biosensor, comprising
   a substrate;
   a waveguide on the substrate;
   a first pair of transducers on the substrate having an acoustic path capable of propagating a first wave therebetween; and
   a second and third pair of transducers fabricated on the substrate, each pair having an acoustic path capable of propagating a second wave therebetween, wherein the first, second, and third acoustic paths intersect creating a center sensing region.

2. The biosensor of claim 1, wherein the substrate is chosen from the group consisting of lithium tantalite and lithium niobate.

3. The biosensor of claim 1, further comprising a sensing film positioned in the sensing region.

4. The biosensor of claim 1, wherein the waveguide is a polystyrene waveguide.

5. The biosensor of claim 1, wherein the acoustic paths are further arranged such that each path is at about a sixty degree angle from the other paths creating a hexagonal shape.

6. The biosensor of claim 1, wherein the first acoustic path lies along an on-axis direction and the plurality of additional delay paths lie in an off-axis directions.

7. The biosensor of claim 1, wherein the acoustic paths lie along each Euler direction.

8. The biosensor of claim 1, wherein the acoustic paths are bi-directional.

9. The biosensor of claim 1, wherein the transducers comprise a plurality of finger pairs.

10. The biosensor of claim 1, wherein the transducers have an aperture of 47λ and a delay path of 197λ.

11. The biosensor of claim 1, wherein the design of the transducer is selected from the group consisting of double split finger, pruned double split finger, and unidirectional double split finger.

12. The biosensor of claim 8, wherein the finger pairs have a periodicity of 40 microns and an aperture width of 200 microns.

13. The biosensor of claim 1, further comprising a power source applied to the transducers.

14. The biosensor of claim 13, wherein the power level applied to the first pair of transducers is about 1 mW and the power level applied to the second and third pairs of transducer is about 12 mW.

15. The biosensor of claim 3, wherein the sensing film is an anti-human I-6 biosensor film.

16. The biosensor of claim 1, wherein the first wave is selected from the group consisting of shear horizontal surface acoustic waves and Love surface acoustic waves and the second wave is a substantially ellipsoidal surface acoustic wave.

17. The biosensor of claim 1, wherein the amplitude of the second wave is greater than the amplitude of the first wave.

18. A method of detecting an analyte in a sample comprising
providing a biosensor having
a substrate;
a waveguide on the substrate;
a first pair of transducers on the substrate having an acoustic path capable of propagating a first wave therebetween;
a second and third pair of transducers fabricated on the substrate, each pair having an acoustic path capable of propagating a second wave therebetween, wherein the first, second, and third acoustic paths intersect to create a center sensing region; and
a sensing film positioned in the center sensing region;
introducing the sensing film to the sample;
generating a sensing wave along the first acoustic path;
monitoring the sensing wave;
generating a removal wave, having a greater amplitude than the sensing wave, along the second and third paths.

19. The method of claim 18, wherein the acoustic paths each have an output signal.

20. The method of claim 18, wherein generating the sensing wave along the first acoustic path is accomplished by applying a power source to the transducers of the first acoustic path.

21. The method of claim 18, wherein monitoring the sensing wave comprises monitoring perturbations of the sensing wave at the transducers.

22. The method of claim 18, wherein generating the removal wave along the second acoustic path is accomplished by applying a power source to the transducers of the second acoustic path.

23. The method of claim 18, wherein generating the removal wave along the third acoustic path is accomplished by applying a power source to the transducers of the third acoustic path.

24. A biosensor, comprising
a substrate;
a first pair of transducers on the substrate having an acoustic path capable of propagating a first wave therebetween;
a second and third pair of transducers fabricated on the substrate, each pair having an acoustic path capable of propagating a second wave therebetween, wherein the first, second, and third acoustic paths intersect creating a center sensing region; and
a power source applied to the transducers, wherein the power level applied to the first pair of transducers is about 1 mW and the power level applied to the second and third pairs of transducer is about 12 mW.

25. The biosensor of claim 24, wherein the substrate is chosen from the group consisting of lithium tantalite and lithium niobate.

26. The biosensor of claim 24, further comprising a waveguide on the substrate.

27. The biosensor of claim 26, wherein the waveguide is a polystyrene waveguide.

28. The biosensor of claim 24, wherein the acoustic paths are further arranged such that each path is at about a sixty degree angle from the other paths creating a hexagonal shape.

29. The biosensor of claim 24, wherein the first acoustic path lies along an on-axis direction and the plurality of additional delay paths lie in an off-axis directions.

30. The biosensor of claim 24, wherein the acoustic paths lie along each Euler direction.

31. The biosensor of claim 24, wherein the acoustic paths are bi-directional.

32. The biosensor of claim 24, wherein the transducers comprise a plurality of finger pairs.

33. The biosensor of claim 32, wherein the finger pairs have a periodicity of 40 microns and an aperture width of 200 microns.

34. The biosensor of claim 24, wherein the transducers have an aperture of 47λ and a delay path of 197λ.

35. The biosensor of claim 24, wherein the design of the transducer is selected from the group consisting of double split finger, pruned double split finger, and unidirectional double split finger.

36. The biosensor of claim 24, further comprising a sensing film positioned in the sensing region.

37. The biosensor of claim 34, wherein the first wave is selected from the group consisting of shear horizontal surface acoustic waves and Love surface acoustic waves and the second wave is a substantially ellipsoidal surface acoustic wave.

38. The biosensor of claim 24, wherein the amplitude of the second wave is greater than the amplitude of the first wave.

39. A biosensor, comprising
a substrate;
a first pair of transducers on the substrate having an acoustic path capable of propagating a first wave therebetween, wherein the first wave is selected from the group consisting of shear horizontal surface acoustic waves and Love surface acoustic waves; and
a second and third pair of transducers fabricated on the substrate, each pair having an acoustic path capable of propagating a second wave therebetween, wherein the first, second, and third acoustic paths intersect creating a center sensing region and wherein the second wave is a substantially ellipsoidal surface acoustic wave.

40. The biosensor of claim 39, wherein the substrate is chosen from the group consisting of lithium tantalite and lithium niobate.

41. The biosensor of claim 39, further comprising a waveguide on the substrate.

42. The biosensor of claim 41, wherein the waveguide is a polystyrene waveguide.

43. The biosensor of claim 39, wherein the acoustic paths are further arranged such that each path is at about a sixty degree angle from the other paths creating a hexagonal shape.

44. The biosensor of claim 39, wherein the first acoustic path lies along an on-axis direction and the plurality of additional delay paths lie in an off-axis directions.

45. The biosensor of claim 39, wherein the acoustic paths lie along each Euler direction.

46. The biosensor of claim 39, wherein the acoustic paths are bi-directional.

47. The biosensor of claim 39, wherein the transducers comprise a plurality of finger pairs.

48. The biosensor of claim 47, wherein the finger pairs have a periodicity of 40 microns and an aperture width of 200 microns.

49. The biosensor of claim 39, wherein the transducers have an aperture of 47λ and a delay path of 197λ.

50. The biosensor of claim 39, wherein the design of the transducer is selected from the group consisting of double split finger, pruned double split finger, and unidirectional double split finger.

51. The biosensor of claim 39, further comprising a power source applied to the transducers.

52. The biosensor of claim 51, wherein the power level applied to the first pair of transducers is about 1 mW and the power level applied to the second and third pairs of transducer is about 12 mW.

53. The biosensor of claim 39, further comprising a sensing film positioned in the sensing region.

54. The biosensor of claim 39, wherein the amplitude of the second wave is greater than the amplitude of the first wave.

55. A method of detecting an analyte in a sample comprising
providing a biosensor having
a substrate;
a first pair of transducers on the substrate having an acoustic path capable of propagating a first wave therebetween;
a second and third pair of transducers fabricated on the substrate, each pair having an acoustic path capable of propagating a second wave therebetween, wherein the first, second, and third acoustic paths intersect to create a center sensing region;
a power source applied to the transducers, wherein the power level applied to the first pair of transducers is about 1 mW and the power level applied to the second and third pairs of transducer is about 12 mW; and
a sensing film positioned in the center sensing region;
introducing the sensing film to the sample;
generating a sensing wave along the first acoustic path;
monitoring the sensing wave;
generating a removal wave, having a greater amplitude than the sensing wave, along the second and third paths.

56. The method of claim 55, wherein the acoustic paths each have an output signal.

57. The method of claim 55, wherein monitoring the sensor wave comprises monitoring perturbations of the sensing wave at the transducers.

58. A method of detecting an analyte in a sample comprising
providing a biosensor having
a substrate;
a first pair of transducers on the substrate having an acoustic path capable of propagating a first wave therebetween, wherein the first wave is selected from the group consisting of shear horizontal surface acoustic waves and Love surface acoustic waves;
a second and third pair of transducers fabricated on the substrate, each pair having an acoustic path capable of propagating a second wave therebetween, wherein the first, second, and third acoustic paths intersect to create a center sensing region; and
a sensing film positioned in the center sensing region;
introducing the sensing film to the sample;
generating a sensing wave along the first acoustic path;
monitoring the sensing wave;
generating a removal wave, having a greater amplitude than the sensing wave, along the second and third paths.

59. The method of claim 58, wherein the acoustic paths each have an output signal.

60. The method of claim 58, wherein generating the sensing wave along the first acoustic path is accomplished by applying a power source to the transducers of the first acoustic path.

61. The method of claim 58, wherein monitoring the sensor wave comprises monitoring perturbations of the sensing wave at the transducers.

62. The method of claim 58 wherein generating the removal wave along the second acoustic path is accomplished by applying a power source to the transducers of the second acoustic path.

63. The method of claim 58, wherein generating the removal wave along the third acoustic path is accomplished by applying a power source to the transducers of the third acoustic path.

* * * * *